United States Patent
Swanson et al.

(10) Patent No.: US 8,135,152 B2
(45) Date of Patent: Mar. 13, 2012

(54) METHOD AND APPARATUS FOR ENVELOPE DETECTION AND ENHANCEMENT OF PITCH CUE OF AUDIO SIGNALS

(75) Inventors: Brett A. Swanson, Meadowbank (AU); Peter J. Blamey, Mt. Waverley (AU); Hugh J. McDermott, Mt. Macedona (AU); James F. Patrick, Roseville (AU)

(73) Assignees: Cochlear Limited, Macquarie University, NSW (AU); The University of Melbourne, Victoria (AU)

( * ) Notice: Subject to any disclaimer, the term of this patent is extended or adjusted under 35 U.S.C. 154(b) by 392 days.

(21) Appl. No.: 12/391,229

(22) Filed: Feb. 23, 2009

(65) Prior Publication Data

US 2009/0161896 A1 Jun. 25, 2009

Related U.S. Application Data

(63) Continuation of application No. 10/526,190, filed as application No. PCT/AU03/01130 on Sep. 2, 2003, now abandoned.

(30) Foreign Application Priority Data

Sep. 2, 2002 (AU) .................................. 2002951165
Aug. 18, 2003 (AU) .................................. 2003904405

(51) Int. Cl.
*H04R 25/00* (2006.01)
*A61N 1/00* (2006.01)
(52) U.S. Cl. ........................................ 381/312; 607/57
(58) Field of Classification Search .................. 381/312; 607/57
See application file for complete search history.

(56) References Cited

U.S. PATENT DOCUMENTS

| 4,028,627 A | | 6/1977 | Cho et al. |
| 4,620,444 A | | 11/1986 | Young |
| 4,918,745 A | * | 4/1990 | Hutchison ............... 607/136 |
| 5,180,931 A | * | 1/1993 | Harada ...................... 327/62 |
| 6,778,858 B1 | * | 8/2004 | Peeters ....................... 607/57 |

OTHER PUBLICATIONS

Graf, R.F. "Encyclopedia of Electronic Circuits," 1991, vol. 3, p. 152, Tab Books.

* cited by examiner

*Primary Examiner* — Brian Ensey
(74) *Attorney, Agent, or Firm* — Kilpatrick, Townsend & Stockton, LLP.

(57) ABSTRACT

A method and apparatus for detecting an envelope of an audio signal, and a method and apparatus for enhancing the pitch cue of an audio signal perceived by a cochlear implant patient where the audio signal is processed and input to an implant device of the recipient. The methods and apparatuses use techniques such as filtering, rectifying, detecting peak values, sampling, resetting, comparing and multiplying various signals to detect the envelope or enhance the pitch cue of the audio signal.

27 Claims, 17 Drawing Sheets

Figure 23: Uniform clock vs Synchronised clock

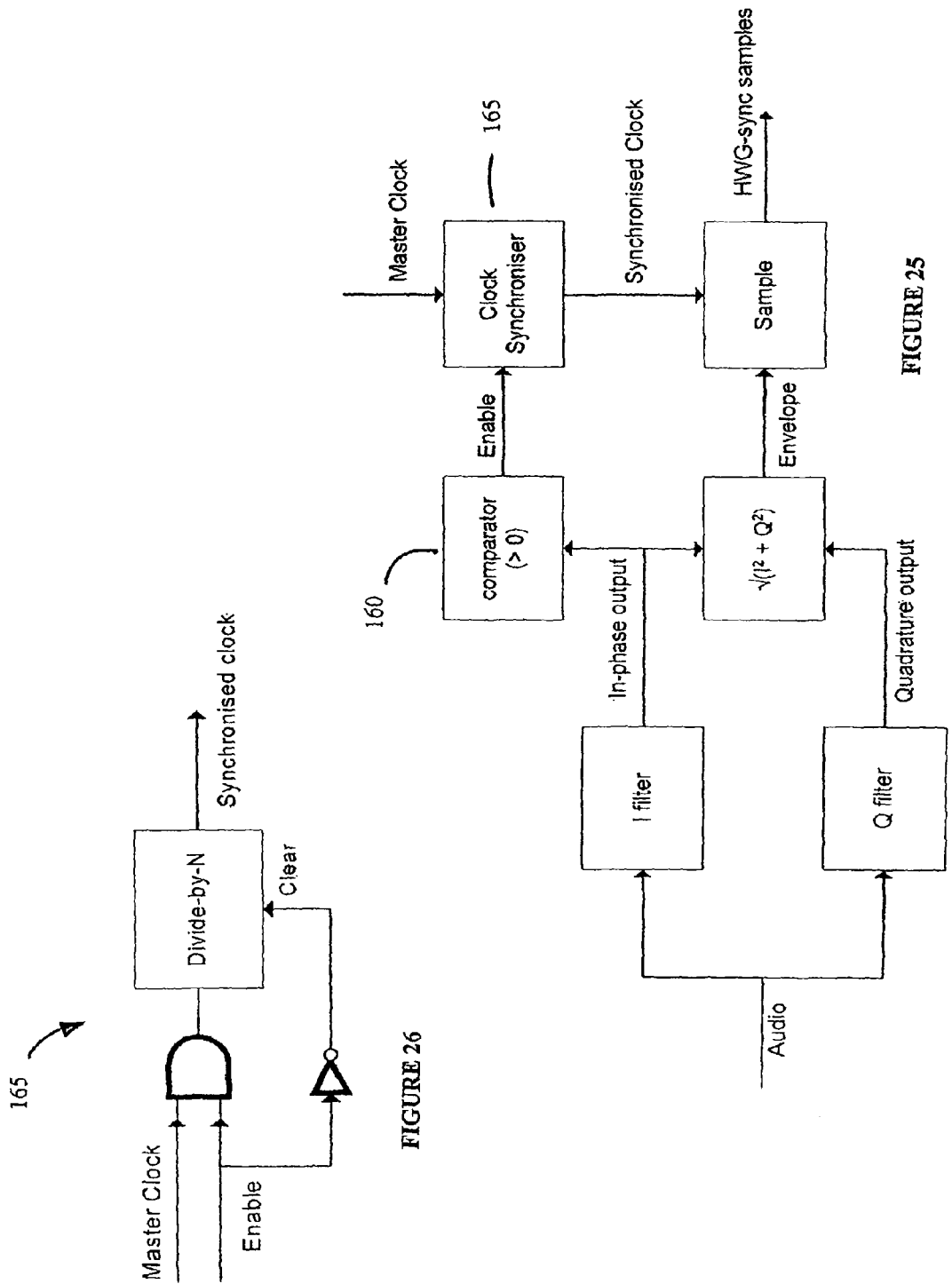

METHOD AND APPARATUS FOR ENVELOPE DETECTION AND ENHANCEMENT OF PITCH CUE OF AUDIO SIGNALS

CROSS-REFERENCE TO RELATED APPLICATIONS

The present application is a continuation of U.S. Utility patent application Ser. No. 10/526,190; filed Jun. 15, 2006, which is a national stage application of PCT Application No. PCT/AU2003/001130, entitled, "Method and Apparatus for Envelope Detection and Enhancement of Pitch Cue of Audio Signal," filed on Sep. 2, 2003, which claims the priority of Australian Patent No. 2002951165, filed on Sep. 2, 2002 and Australian Patent No. 2003904405, filed on Aug. 18, 2003. The entire disclosure and contents of the above applications are hereby incorporated by reference herein.

BACKGROUND

1. Field of the Invention

The present invention relates to hearing prosthesis and to sound processing devices and methods associated with hearing prosthesis. In particular, the present invention relates to an apparatus and method of envelope detection that is simple to implement in both analog circuitry or digital signal processing and assists cochlear implant recipients to better perceive changes in the amplitude of speech than is currently the case. Furthermore, the invention relates to an apparatus and method for enhancing the pitch cue of an audio signal perceived by a cochlear implant recipient.

2. Background of the Invention

In many people who are profoundly deaf, the reason for deafness is absence of, or destruction of, the hair cells in the cochlea which transduce acoustic signals into nerve impulses. These people are unable to derive suitable benefit from conventional hearing aid systems, no matter how loud the acoustic stimulus is made, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, also in the name of the applicant and the contents of which are incorporated herein by reference, provides a description of one type of traditional cochlear implant system.

Typically, cochlear implant systems have consisted of essentially two components, an external component commonly referred to as a processor unit and an internal implanted component commonly referred to as a receiver/stimulator unit. Traditionally, both of these components have cooperated together to provide the sound sensation to a user.

The external component has traditionally consisted of a microphone for detecting sounds, such as speech and environmental sounds, a speech processor that converts the detected sounds, particularly speech, into a coded signal, a power source such as a battery, and an external transmitter coil.

The coded signal output by the speech processor is transmitted transcutaneously to the implanted stimulator/receiver unit situated within a recess of the temporal bone of the user. This transcutaneous transmission occurs via the external transmitter coil which is positioned to communicate with an implanted receiver coil provided with the stimulator/receiver unit.

This communication serves two essential purposes, firstly to transcutaneously transmit the coded sound signal and secondly to provide power to the implanted stimulator/receiver unit. Conventionally, this link has been in the form of a radio frequency (RF) link, but other such links have been proposed and implemented with varying degrees of success.

The implanted stimulator/receiver unit traditionally includes a receiver coil that receives the coded signal and power from the external processor component, and a stimulator that processes the coded signal and outputs a stimulation signal to an intracochlear electrode assembly which applies the electrical stimulation directly to the auditory nerve producing a hearing sensation corresponding to the original detected sound.

Traditionally, the external componentry has been carried on the body of the user, such as in a pocket of the user's clothing, a belt pouch or in a harness, while the microphone has been mounted on a clip behind the ear or on the lapel of the user.

More recently, due in the main to improvements in technology, the physical dimensions of the speech processor have been able to be reduced allowing for the external componentry to be housed in a small unit capable of being worn behind the ear of the user. This unit allows the microphone, power unit and the speech processor to be housed in a single unit capable of being discretely worn behind the ear, with the external transmitter coil still positioned on the side of the user's head to allow for the transmission of the coded sound signal from the speech processor and power to the implanted stimulator unit. It is envisaged that with further technological advancements the system components will be able to be fully implanted within the head of the recipient, providing a totally invisible device.

As the ability to perceive sound is of fundamental importance to cochlear implant recipients, the ability to reproduce sound and the percepts of speech via electrical stimulation using a cochlear prosthesis is one of the major challenges of this technology. It is the speech processor that provides the link between the acoustic representation of speech and the pattern of neural discharges which the stimulator of the implant is able to induce, and which the recipient experiences as hearing sensations. Many speech-processing strategies such as Continuous Inter-leaved Sampling (CIS), and those based on spectral maxima SPEAK and ACE, have been proposed to improve the quality of the sensation as perceived by the recipient, in a number of different sound environments.

These strategies utilise envelope detection for processing the output of a series of filters, however a disadvantage of such systems is that the output of the envelope detector typically includes a large amount of ripple and/or the desired envelope becomes excessively smeared out. This has the disadvantage of adversely affecting the temporal cues that are important in consonant perception. Other implementations of the strategies may result in the output having a ripple which is aliased causing the stimulation amplitude to vary with a frequency which is not present in the input sound. Such a ripple can modulate at a beat frequency which can give erroneous pitch cues to the implant recipient.

Another prior system called quadrature envelope detection, although producing an envelope which substantially contains no ripple and is not smeared out, has the disadvantage that it is complex and requires twice as many band pass filters as there are frequency channels which results in additional cost and complexity. Furthermore, the need to provide the function of squaring and square root operations is generally not practical in analogue circuitry.

In normal hearing, the inner hair cells only respond to movement of the basilar membrane in one direction. They tend to fire in phase with the basilar membrane response. This is known as "phase-locking"; it preserves the timing content of the basilar membrane response, and it is believed to be important for pitch perception. At high stimulation rates, the fine timing content generally has not been taken into account and therefore implant recipients have not been able to adequately perceive pitch in an audio signal. The present invention substantially preserves the fine timing content of the band-pass filter outputs, and provides an additional pitch cue to the cochlear implant recipient. It requires high stimulation rates.

The present invention is therefore related to improving the manner in which an audio signal is processed so that the quality of sound reproduced via the electrical stimulation is substantially maintained.

SUMMARY OF THE INVENTION

According to a first aspect of the invention, there is provided a method of detecting an envelope of an audio signal comprising the steps of: filtering said audio signal to produce a filtered audio signal; rectifying the filtered audio signal to produce a rectified signal; detecting the peak values of the rectified signal to produce a detected signal; sampling the detected signal at predetermined time intervals to produce samples; and resetting the detected signal immediately after sampling.

According to a second aspect of the invention there is provided a method of detecting an envelope of an audio signal comprising the steps of: filtering the audio signal into multiple filtered audio signals; rectifying each of the multiple filtered audio signals into respective multiple rectified signals; detecting peak values of each of the multiple rectified signals to produce detected signals; sampling each of the detected signals at predetermined time intervals to produce samples; and resetting each of the detected signals immediately after sampling.

Preferably, the rectifying step involves using either half wave rectification (HWR) or full wave rectification (FWR). Preferably, each of the detected peak values remain at a substantially constant value prior to sampling. Preferably, after each sample the method further comprises the step of resetting the detected signal or detected signals, and more particularly resetting the detecting signal or detected signals substantially to zero.

The sampling rate may be relatively low compared to the frequency components in the filtered audio signal. Preferably the audio signal is input to a cochlear implant device.

According to a third aspect of the invention, there is provided apparatus for detecting an envelope of an audio signal comprising: means for filtering the audio signal to produce a filtered audio signal; means for rectifying the filtered audio signal to produce a rectified signal; means for detecting the peak values of the rectified signal to produce a detected signal; means for sampling the detected signal at predetermined time intervals to produce samples; and means for resetting the means for detecting immediately after sampling, such that the detected signal is reset immediately following sampling.

According to a fourth aspect of the invention there is provided apparatus for detecting an envelope of an audio signal comprising: means for filtering the audio signal into multiple filtered audio signals; means for rectifying each of the multiple filtered audio signals into respective multiple rectified signals; means for detecting the peak values of each of the multiple rectified signals to produce detected signals; means for sampling each of the detected signals at predetermined time intervals to produce samples; and means for resetting the means for detecting immediately after sampling, such that each of the detected signals are reset immediately following sampling.

The present invention through processing the filtered signal in one or more frequency ranges of interest, provides an improved method of estimating the amount of energy present in a frequency band used by a cochlear implant.

According to a fifth aspect of the invention there is provided a method of enhancing the pitch cue of an audio signal perceived by a cochlear implant recipient, wherein the audio signal is processed and input to an implant device of the recipient, the method comprising the steps of: filtering the audio signal to produce a filtered audio signal; half-wave rectifying the filtered audio signal to produce a half-wave rectified signal; and sampling the half-wave rectified signal at predetermined time intervals.

This is in contrast with the prior art which aims to produce a smooth envelope signal which varies slowly compared to the centre frequency of the filter, thereby removing all of the fin timing structure of the filtered signal.

According to a sixth aspect of the invention there is provided a method of enhancing the pitch cue of an audio signal perceived by a cochlear implant recipient, wherein the audio signal is processed and input to an implant device of the recipient, the method comprising the steps of: filtering the audio signal to produce a filtered audio signal; envelope detecting the filtered audio signal to produce an envelope detected signal; comparing the filtered audio signal to produce a gating signal having one of two Boolean states; multiplying the gating signal with the envelope detected signal to produce a multiplied signal; and sampling the multiplied signal at predetermined time intervals.

The step of envelope detection may involve quadrature envelope detection such that the envelope detected signal is produced using In-phase and quadrature phase filtered components of the audio signal. The gating signal may be produced from an in-phase filtered component of the audio signal. The filtering step may involve using quadrature filters such that the audio signal is filtered into in-phase and quadrature-phase components.

For sampling at high frequencies, the method may further comprise the step of detecting the peaks of the multiplied signal and resetting the multiplied signal, then sampling the multiplied signal at predetermined time intervals.

According to a seventh aspect of the invention there is provided a method of enhancing the pitch cue of an audio signal perceived by a cochlear implant recipient, wherein the audio signal is processed and input to an implant device of the recipient, the method comprising the steps of: filtering the audio signal to produce a filtered audio signal; envelope detecting the filtered audio signal to produce an envelope detected signal; comparing the filtered audio signal to produce a gating signal having one of two Boolean states; multiplying the gating signal with the envelope detected signal to produce a multiplied signal; detecting the peak values of and resetting the multiplied signal to produce a peak detected and reset multiplied signal.

The step of filtering may involve using quadrature filters such that the audio signal is filtered into in-phase and quadrature-phase components. The step of envelope detection may be quadrature envelope detection such that the envelope detected signal is based on the in-phase and quadrature-phase filtered components of the audio signal.

Thus at high frequencies, preferably more than four times the audio frequency, the method conveys fine timing content of the filter output signal giving an enhanced pitch cue to the implant recipient. Whilst at lower frequencies, preferably less than twice the audio frequency, the method implements envelope detection.

The method may comprise applying the peak detected and reset multiplied signal to apical electrode channels and to basal electrode channels.

The method may comprise the step of sampling at relatively high frequencies (high stimulation rates) for use by apical electrode channels to obtain enhanced pitch cues, corresponding to responses to low frequency signals.

The method may further comprise the step of sampling at relatively low frequencies (low stimulation rates) using envelope detection applied to basal electrode channels, corresponding to responses to high frequency signals.

According to an eighth aspect of the invention, there is provided an apparatus for enhancing the pitch cue of an audio signal perceived by a cochlear implant recipient, the audio signal being processed and input to an implant device of the recipient, the apparatus comprising: means for filtering the audio signal to produce a filtered audio signal; means for half-wave rectifying the filtered audio signal to produce a half-wave rectified signal; and means for sampling the half-wave rectified signal at predetermined time intervals.

According to a ninth aspect of the invention, there is provided apparatus for enhancing the pitch cue of an audio signal perceived by a cochlear implant recipient, the audio signal being processed and input to an implant device of the recipient, the apparatus comprising: means for filtering the audio signal to produce the filtered audio signal; means for envelope detecting the filtered audio signal to produce an envelope detected signal; comparator means for producing a gating signal having one of two Boolean states; means for multiplying the gating signal with the envelope detected signal to produce a multiplied signal; and means for sampling the multiplied signal at predetermined time intervals.

According to a tenth aspect of the invention, there is provided apparatus for enhancing the pitch cue of an audio signal perceived by a cochlear implant recipient, the audio signal being processed and input to an implant device of the recipient, the apparatus comprising: means for filtering the audio signal to produce a filtered audio signal; means for envelope detecting the filtered audio signal to produce an envelope detected signal; comparator means for producing a gating signal having one of two Boolean states; means for multiplying the gating signal with the envelope detected signal to produce a multiplied signal; and means for detecting the peak values of and resetting the multiplied signal to produce a peak detected and reset multiplied signal.

The envelope detection means may include quadrature envelope detection means. The filter means may include in-phase filter means and quadrature-phase filter means. The apparatus may further include circuit means for producing the envelope detected signal based on values of the outputs to the in-phase and quadrature-phase filter means. The comparator means may have at its input, the output from the in-phase filter means.

According to an eleventh aspect of the invention there is provided a method of enhancing the pitch cue of an audio signal perceived by a cochlear implant recipient, wherein the audio signal is processed and input to an implant device of the recipient, the method comprising the steps of: filtering the audio signal to produce a filtered audio signal; and sampling the filtered audio signal to produce samples; wherein the samples are synchronized with the filtered audio signal.

Preferably the sampling step involves using a clock synchroniser comprising bursts of pulses separated by a fixed time interval with the leading pulse in each burst of pulses being synchronised to the phase of the filtered audio signal. Preferably the leading pulse occurs at a fixed time interval after the rising zero crossing of the filtered audio signal, such that only positive cycles of the audio wave form are sampled.

According to a twelfth aspect of the invention there is provided a method of enhancing the pitch cue of an audio signal perceived by a cochlear implant recipient, wherein the audio signal is processed and input to an implant device of the recipient, the method comprising the steps of: filtering the audio signal to produce a filtered audio signal; envelope detecting the filtered audio signal to produce an envelope detected signal; and sampling the envelope detected signal; wherein the samples of the envelope detected signal are synchronised with the filtered audio signal.

Preferably the sampling step involves using a clock synchroniser that generates bursts of clock pulses separated by a fixed time interval with the leading pulse in each burst of pulses being synchronised to the phase of a portion of the filtered audio signal. The step of envelope detection may involve quadrature envelope detection with the leading pulse in each burst of pulses of the clock synchroniser being synchronised to the in-phase filtered signal. Preferably the leading pulse occurs at a fixed time interval after the rising zero crossing of the filtered audio signal, such that only positive cycles of the audio wave form are sampled.

According to a thirteenth aspect of the invention there is provided an apparatus for enhancing the pitch cue of an audio signal perceived by a cochlear implant recipient, the audio signal being processed and input to an implant device of the recipient, the apparatus comprising: means for filtering the audio signal to produce a filtered audio signal; and means for sampling the filtered audio signal at predetermined time intervals to produce samples; wherein the samples are synchronised with the filtered audio signal.

According to a fourteenth aspect of the invention there is provided apparatus for enhancing the pitch cue of an audio signal perceived by a cochlear implant recipient, the audio signal being processed and input to an implant device of the recipient, the apparatus comprising: means for filtering the audio signal to produce a filtered audio signal; means for envelope detecting the filtered audio signal to produce an envelope detected signal; and means for sampling the envelope detected signal to produce samples; wherein the samples of the envelope detected signal are synchronised with the filtered audio signal.

According to a fifteenth aspect of the invention there is provided, in a multiple channel cochlear implant system permitting sequential stimulation, a method of enhancing the pitch cue of an audio signal perceived by a cochlear implant recipient, wherein the audio signal is processed and input to an implant device of the recipient, the method comprising the steps of: filtering the audio signal to produce a filtered audio signal; sampling the filtered audio signal to produce samples; and synchronising the samples of the filtered audio signal using a selection means and a series of master clock pulses, such that on each master clock pulse no more than one channel is selected by the selection means.

Preferably each channel has a low to high transition on a channel enable signal. Each channel enable signal is preferably input to the selection means and passed through the selection means with controllable delay on each channel. Preferably where more than one channel enable signal goes high on a single master clock pulse, one channel is selected as previously described, with the remaining channels delayed by successive master clock periods.

According to a sixteenth aspect of the invention there is provided a method of enhancing the pitch cue of an audio signal perceived by a cochlear implant recipient, wherein the audio signal is processed and input to an implant device of the recipient, the method comprising the steps of: filtering the audio signal to produce a filtered audio signal; half-wave rectifying the filtered audio signal to produce a half-wave rectified signal; detecting the peak values of the half-wave rectified signal and resetting the detected peak values to produce a reset detected signal; and sampling the reset detected signal at predetermined time intervals.

According to a seventeenth aspect of the invention there is provided apparatus for enhancing the pitch cue of an audio signal perceived by a cochlear implant recipient, the audio signal being processed and input to an implant device of the recipient, the apparatus comprising: means for filtering the audio signal to produce a filtered audio signal; means for half-wave rectifying the filtered audio signal to produce a half-wave rectified signal; means for detecting the peak values of the half-wave rectified signal and resetting the detected peak values to produce a reset detected signal; and means for sampling the reset detected signal at predetermined time intervals.

It is to be understood that any of the embodiments described in terms of acting on an audio signal to produce a filtered or rectified signal can be extended to the case of filtering the audio signal into multiple filtered audio signals and rectifying each of the multiple filtered audio signals into respective multiple rectified signals. Furthermore, a number of detected signals can be sampled and reset or a number of rectified signals can be sampled. Thus generally it is to be understood that multiple signals derived from the original audio signal and acted upon, such as sampling, rectifying, detecting, filtering, multiplying, comparing are included as further embodiments.

BRIEF DESCRIPTION OF THE DRAWINGS

By way of example only, preferred embodiments of the invention will now be described with reference to the accompanying drawings, in which:

FIG. 25 is a block diagram of a circuit arrangement of the HWG-sync embodiment of the present invention; and FIG. 26 is a clock synchroniser as used with the embodiments described in relation to FIGS. 23 to 25.

DETAILED DESCRIPTION

Figure 1:
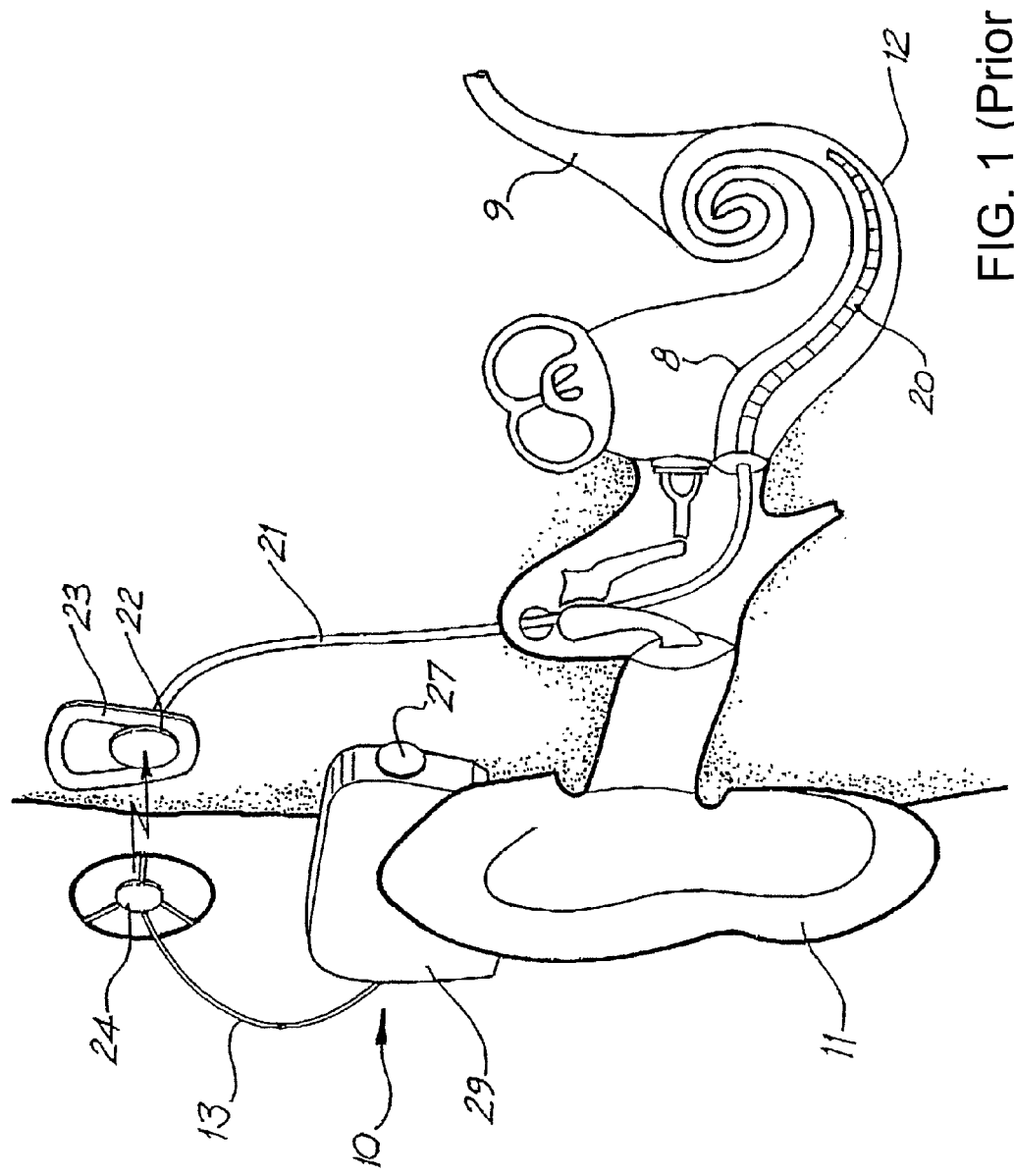
FIG. 1 is a pictorial representation of a conventional cochlear implant system.

Before describing the features of the present invention, it is appropriate to briefly describe the construction of one type of known cochlear implant system with reference to FIG. 1.

Known cochlear implants 10 typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 11 and is held in place behind the outer ear 11 via an ear-hook arrangement (not shown). Alternative versions may be worn on the body. Attached to the speech processor 29 is a transmitter coil 24 that transmits electrical signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 and the nerve cells within the cochlea 12 thereby stimulating the auditory nerve 9. The operation of such a device is described, for example, in U.S. Pat. No. 4,532,930.

Figure 2:
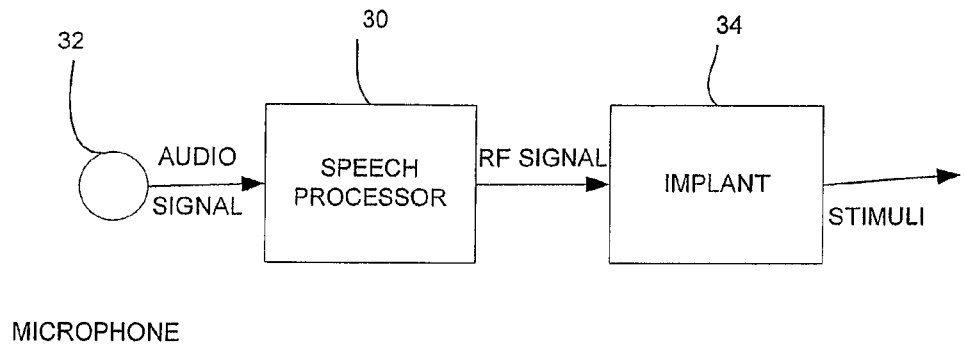
FIG. 2 is a block diagram showing the basic function of a speech processor of a cochlear implant system.

In order to appreciate the basic function of a speech processor 30, such as that shown in FIG. 1, reference is made to FIG. 2. As is shown, the speech processor 30 takes an audio signal (usually from a microphone 32) and processes this signal according to a particular speech processing strategy, to produce a signal that contains stimulation information for an implant 34. Conventionally, this signal is an RF signal that is transcutaneously transmitted to the implant 34.

Figure 3:
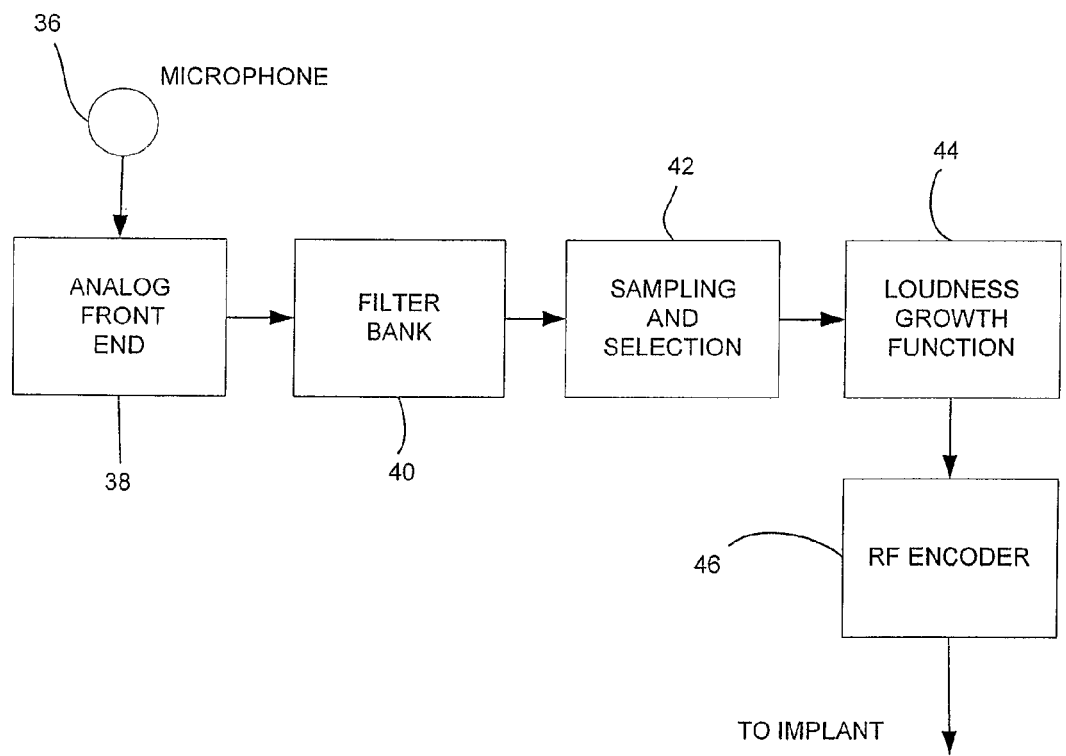
FIG. 3 is a block diagram of the overall signal flow of a conventional speech processing strategy.

FIG. 3 represents an example of a typical block diagram of speech processing in relation to cochlear implants. As is shown, a microphone 36 detects an audio signal with this signal being received by an analog front end 38. The analog front end 38, or audio pre-processor, typically includes a preamplifier that amplifies the very low signal from the microphone 36 to a level which can be easily handled by the rest of the signal processing. This analog front end 38 may also include user sensitivity signals to assist in the pre-processing, such as gain controls and sensitivity controls which can be set by the user to desirable settings.

The next processing stage is a filter bank 40, which typically consists of a set of band-pass filters that cover the input frequency range. Each filter has a different centre frequency allowing signals in one bands of frequencies to pass through whilst other frequencies are blocked. The frequency bands may be based on critical bands, for example these bands may be roughly linearly spaced below 1000 Hz, and logarithmically spaced above 1000 Hz. Each filter may be allocated to one channel (or pair of electrodes) and as a result the number of filters may be equal to the number of channels. The output of this processing stage is the envelopes of the filtered signals, with the envelope being an estimate of the instantaneous power in the corresponding spectral band. An envelope detector processes the output of each filter to provide an estimate of the amount of energy in the frequency band. By sampling the envelope of each filter, the amplitude of the electrical stimulation pulses can be controlled.

Following the filter bank stage 40 where a continuous set of output signals are provided for each band-pass filter employed, the Filter Bank outputs must then be sampled so that a sequence of stimulation frames can be determined. This is performed by a sample and selection unit 42. There are a number of strategies which employ different sampling and selection techniques at this stage of the signal processing, for example, CIS, SPEAK and ACE previously referred to. As each filter is usually allocated to one channel, the filter output sampling rate can be the same as the stimulation rate on that channel.

In the CIS strategy, all filter bank output samples are selected and the corresponding channels are then stimulated sequentially. In the SPEAK and ACE strategies, a subset of channels is selected for stimulation with the channels selected being those that have the largest envelope amplitude at the sampling time.

The final stage of processing is the amplitude mapping stage, referred to as the loudness growth function 44. In this stage, the dynamic range of the envelope signal is compressed by a loudness growth function 44 so that all sounds are mapped between the threshold level (T) and the maximum comfort level (C) of the channel to ensure that delivery of the stimulus is detected at the appropriate sound intensity level by the user.

As is shown in FIG. 3, this signal can then be RF encoded through encoder 46 and sent to the implanted stimulator for delivery via the intracochlear electrodes.

As can be appreciated in the above summary of speech processing strategies, at the heart of all the strategies is a filterbank, which splits the sound into a number of frequency bands. Therefore a fundamental aspect of such speech processing strategies is the function of the envelope detector of each filter which provides an estimate of the amount of energy present in each frequency band. It is in this regard that the present invention relates.

Figure 4:
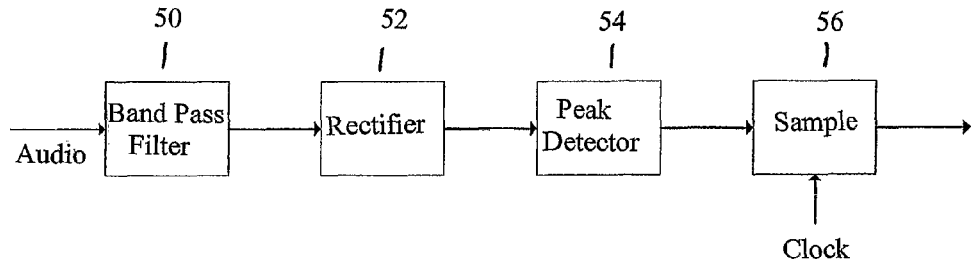
FIG. 4 is a block diagram of a prior art envelope detection method.

In the prior art, a number of different methods of detecting the envelope of each filter have been proposed. One such prior art method is shown in FIGS. 4 and 5, which utilises a rectifier and peak detector.

In this method a band pass filter (BPF) 50 receives an audio input signal. In FIG. 5 and each of the examples that follow, this audio input signal is shown as a short burst of a 350 Hz pure tone (uppermost signal), although it should be appreciated that this input audio signal could be a sound signal as detected by a microphone. In the example shown, the BPF has a centre frequency of 375 Hz and the output of the BPF is shown in FIG. 5.

Figure 5:
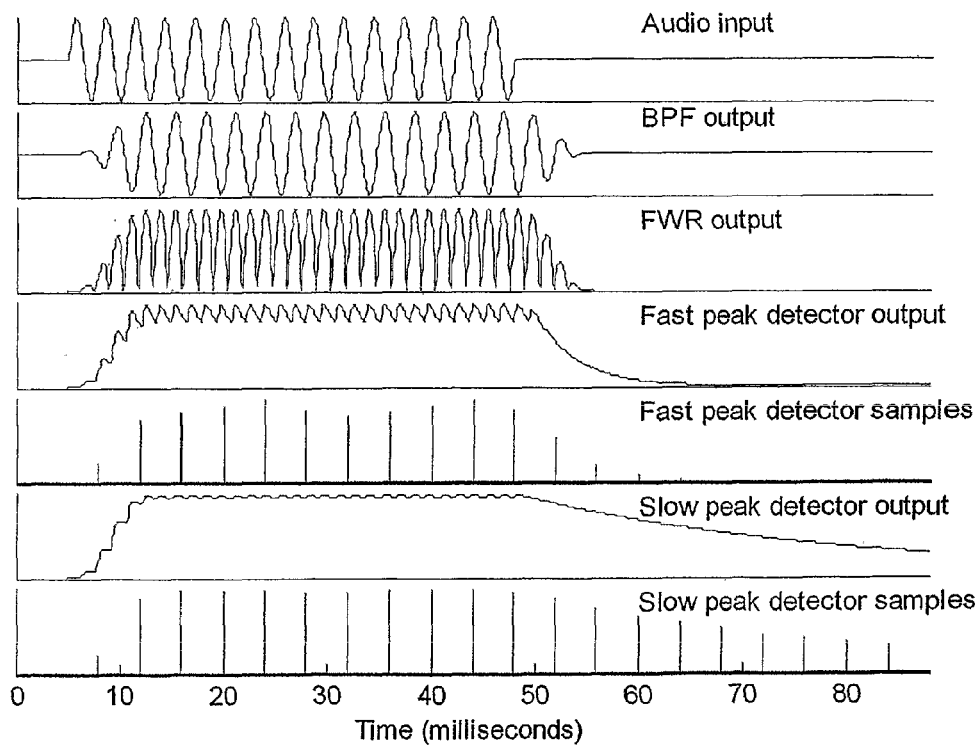
FIG. 5 is a graphical representation of the signal flow of the prior art envelope detection method of FIG. 4.

In order to detect the envelope of this filter the signal is passed through a rectifier 52, such as a full wave rectifier (FWR), the output of which is also shown in FIG. 5. This signal is then passed through a Peak Detector 54 that operates so that when its input signal attempts to rise above its output signal, its output signal follows its input signal; and when the input signal falls below the output signal, the output signal gradually decays. In order for this system to work satisfactorily, a compromise must be made in choosing the decay time constant. In FIG. 5 a fast peak detector output is shown that is obtained when the decay time is short. The disadvantage here is that the output has a large amount of ripple, as can be clearly seen in the signal. A slow peak detector output is also shown that is obtained when the decay time is long. This reduces the ripple, as is evident in the bottom signal of FIG. 5, but it causes the desired envelope to be excessively smeared out. This may adversely affect the temporal cues that are important in consonant perception.

In order to derive the amplitude of the electrical stimulation pulses associated with the audio signal, the output of the peak detector is sampled by sampler 56. In a preferred embodiment, the sample rate is equal to the channel stimulation rate, and in this example the stimulation rate is 250 Hz. FIG. 5 shows the output samples for both the fast and slow peak detectors, wherein each sample is shown by a vertical line. With full-wave rectification, the ripple has twice the frequency of the BPF output. Because the stimulation rate is lower than this, the ripple is aliased and causes the stimulation amplitude to vary at a frequency not present in the input sound. This modulation is an artefact of the processing and may be confused with the actual modulation of the envelope of a voiced speech sound thereby distorting the sound perceived by the implant recipient.

Figure 6:
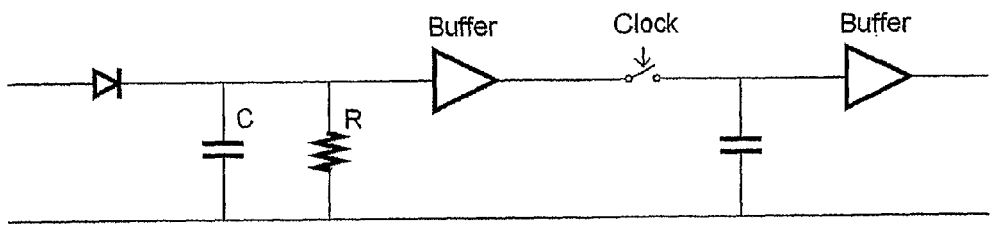
FIG. 6 is a circuit diagram of the prior art envelope detection method of FIG. 4.
Figure 7:
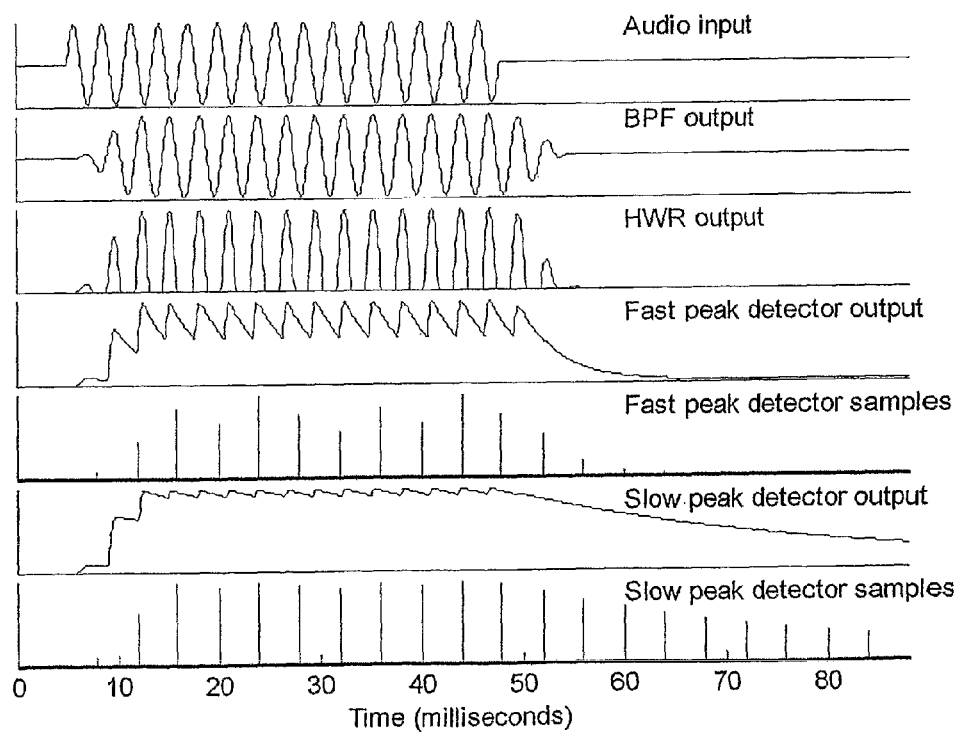
FIG. 7 is a graphical representation of the signal flow of the prior art envelope detection method of FIG. 4 with the full-wave rectifier replaced with a half-wave rectifier.

Instead of a full-wave rectifier used in the prior art system discussed above, this may be replaced by a half-wave rectifier. Furthermore, the half-wave rectifier and peak detector functions can be combined into one circuit. A simple embodiment of this, widely used in AM radio receivers, is shown in FIG. 6. In this example the decay time constant T is determined by the relationship, T=RC. As can be seen clearly in FIG. 7, using a half-wave rectifier instead of a full-wave rectifier increases the amplitude of the ripple, and thus causes more distortion of the envelope samples.

Both of the above mentioned prior art systems may also be implemented digitally. In this case there are two sample rates: the processing sample rate (which is generally equal to the analog-to-digital converter sample rate) and the output sample rate (which is the channel stimulation rate). A digital signal processor may implement the peak detector and sample functions according to the following pseudo-code:

| Variables: | |
|---|---|
| in: | Input signal (from rectifier). |
| clock: | Boolean clock signal indicating when an output sample should be taken. |
| peak: | Internal peak storage (initialised to 0). |
| out: | Output sample. |
| Constants: | |
| decay: | Fraction between 0 and 1 that controls the decay time. |

```
if (in > peak)
    peak = in
else
    peak = peak * decay
if (clock)
    out = peak
```

Figure 8:
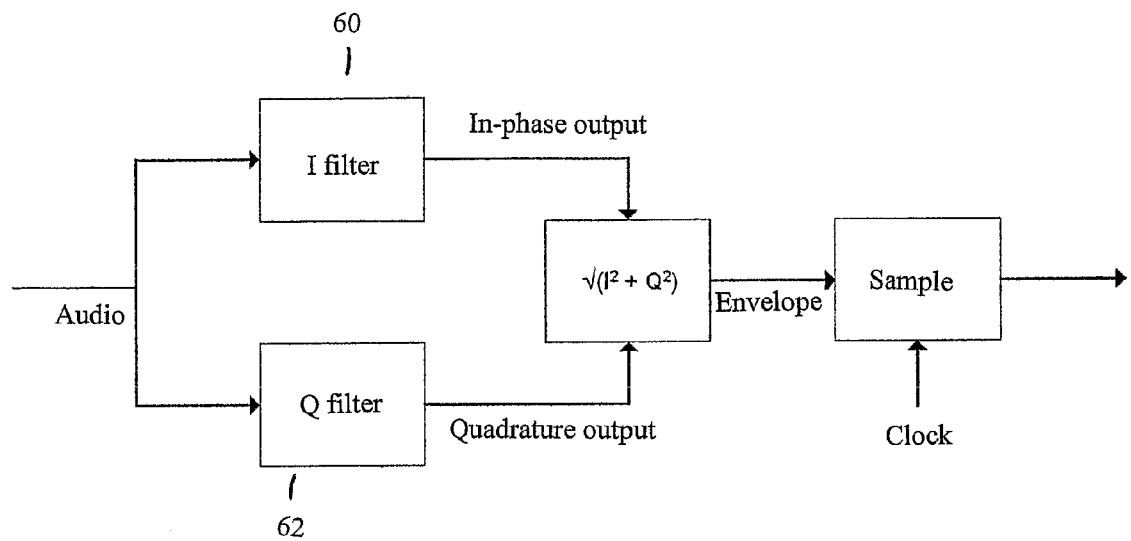
FIG. 8 is a block diagram of an alternative prior art envelope detection method.

Another prior art method of envelope detection is referred to as quadrature envelope detection, and a block diagram of this method is shown in FIG. 8. As is shown, in this scheme, each frequency channel contains a pair of band-pass filters. The first filter is known as the in-phase filter (I filter) 60, and may be the same as that used in the prior art system discussed above. The second filter is known as the quadrature filter (Q filter) 62, and has the same magnitude response as the In-phase filter, but its phase response differs by 90 degrees. If we denote the output of the In-phase filter as I, and the output of the quadrature filter as Q, the envelope E is given by:

$$E = \text{square root of } (I^2 + Q^2)$$

Figure 9:
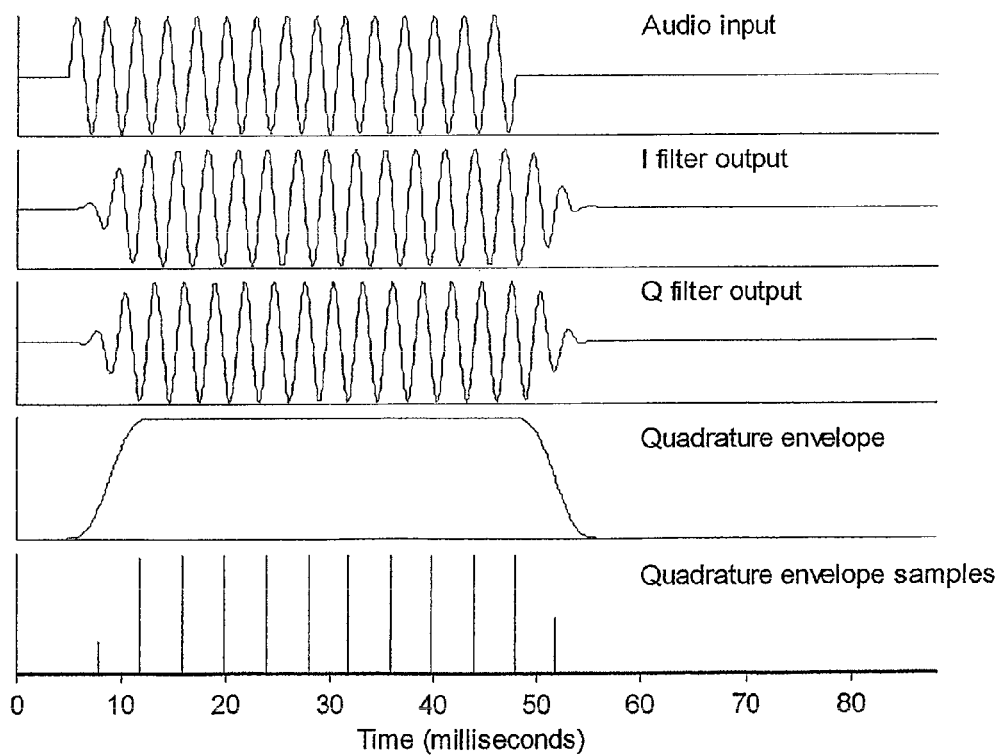
FIG. 9 is a graphical representation of the signal flow of the prior art envelope detection method of FIG. 8.

The equivalent signals of this method are shown in FIG. 9 and it is clearly evident that this method produces an envelope containing no ripple and which is not smeared out, as is the case in each of the previously described methods. However, this method does have the disadvantage that it is complex and requires twice the number of band pass filters than frequency channels. Furthermore, the implementation of the squaring and square root operations is not practical in analog circuitry.

Therefore, the present invention provides a method of envelope detection that minimises the effect of ripple without smearing out the envelope and which does not require overly complex processing that is not practical in analog circuitry, in three different ways.

Figure 10:
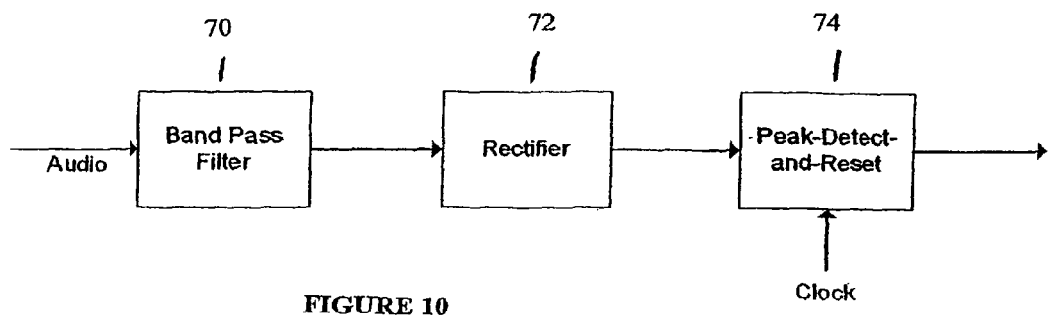
FIG. 10 is a block diagram of the envelope detection method according to one aspect of the present invention.

FIG. 10 illustrates the first method of implementing the system of the present invention, which is applicable for strategies that use a low sample rate (i.e. channel stimulation rate). The SPEAK processing strategy developed by the present applicant is such a strategy, using a channel stimulation rate of 250 Hz. Such strategies employing a low stimulation rate have the advantage that power consumption of the system is minimised.

This method employs an envelope detector comprising a rectifier 72 and a peak-detect-and-reset stage 74 and is applicable when the sample rate is low compared to the audio frequencies that are passed by the band-pass filter 70. Results have shown that in such instances the present invention acts as an envelope detector with performance comparable to that of quadrature envelope detection described above, but with a much lower complexity, comparable to prior art methods that employ rectifiers and peak detectors.

Figure 11:
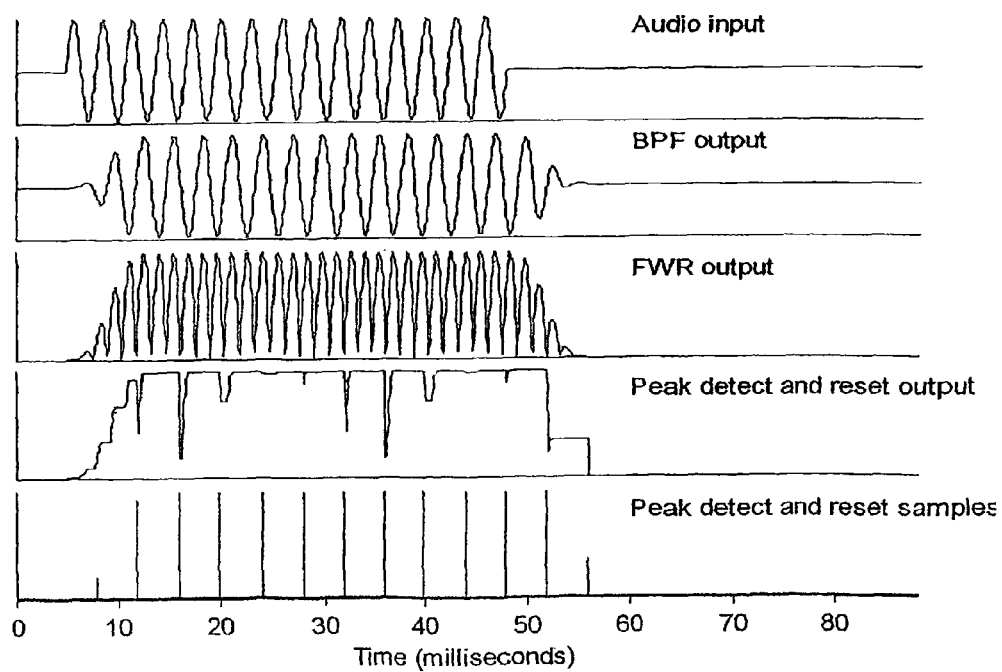
FIG. 11 is a graphical representation of the signal flow of one aspect of the present invention using full-wave rectification.

As shown in FIG. 10, the audio signal is passed through a band pass filter 70, with the resulting signal being passed through rectifier 72, such as a full-wave rectifier (FWR), as is shown in FIG. 11. This signal is then processed by a peak-detect-and-reset stage 74 which combines both the peak detection and sampling operations. This stage operates in a manner such that when the received input signal attempts to rise above the output signal, the output signal follows the input signal, and when the input signal falls below the output signal, the output signal holds its previous value (without decay), with the addition that upon the activation of the clock signal causes the output signal to be sampled and then momentarily set to zero.

Figure 12:
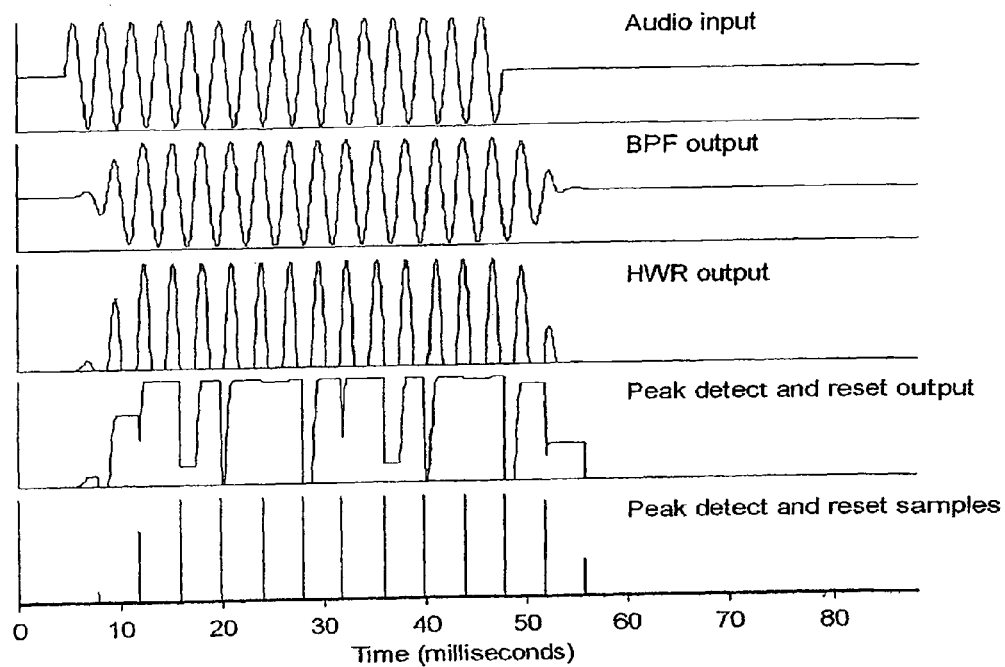
FIG. 12 is a graphical representation of the signal flow of one aspect of the present invention using half-wave rectification.

In the event that the above system uses a FWR, there must be at least one half-cycle of the FWR output between samples, i.e. the sample rate must be less than twice the lowest frequency passed by the BPF. This means that the peak detector always reaches the maximum value of the FWR output before the next sampling time. For a constant amplitude audio tone, the output samples will also be steady in amplitude, without any ripple, aliasing or smearing of the envelope. The use of a half wave rectifier (HWR) is shown in FIG. 12, and in this case, it is important that the sample rate is less than the lowest frequency passed by the BPF.

Figure 13:
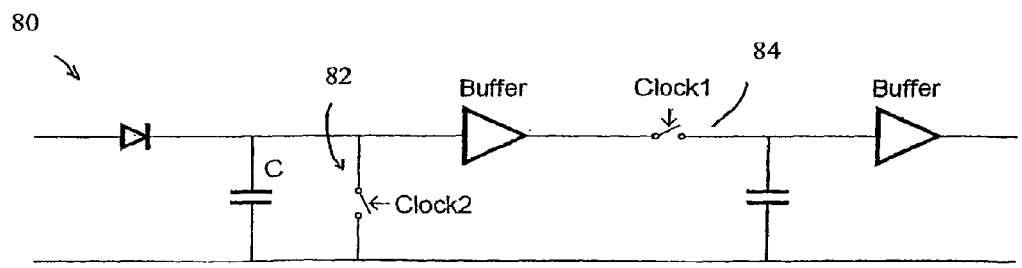
FIG. 13 is a circuit showing one aspect of the present invention using half wave rectification and Peak-Detect-and-Reset.

One simple embodiment of the present invention is shown in the circuit 80 of FIG. 13. This embodiment is similar to the prior art circuit shown in FIG. 6, however the resistor (R) has been replaced with a reset switch 82. In this embodiment, this reset switch 82 closes just after the sampling switch 84 opens. In a two-phase clocking system, the sampling clock (clock 1) to operate switch 84 would be derived from a phase 1 of the master clock, and the reset clock (clock 2) to operate switch 82 would be derived from phase 2 of the master clock.

It is also possible to implement the peak-detect-and-reset function of the present invention digitally and this may be done via a digital signal processor according to the following pseudo-code:

| Variables: | |
|---|---|
| in: | Input signal (from rectifier). |
| clock: | Boolean clock signal indicating when an output sample should be taken. |
| peak: | Internal peak storage (initialised to 0). |
| out: | Output sample. |

```
if (in > peak)
    peak = in
if (clock)
    out = peak
    peak = 0
```

The second method of implementing the system of the present invention is to use very high sample rates and as such is applicable for strategies that use high stimulation rates.

Figure 14:
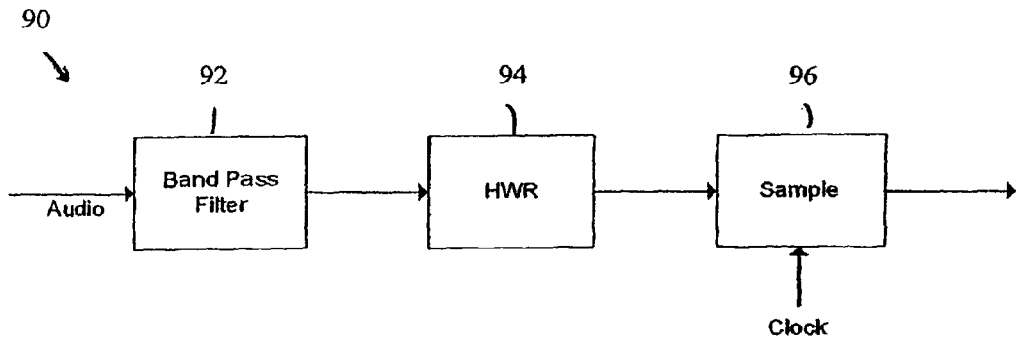
FIG. 14 is a block diagram of an envelope detection method according to a second aspect of the present invention.

According to this embodiment of the present invention there is provided a circuit 90 shown in FIG. 14 wherein each filter 92 is followed by a half-wave rectifier (HWR) 94, and then sampled by sample unit 96.

The phase responses of the individual filters 92 in the filterbank are designed so that when a pure tone is applied, all of the filters that pass that frequency have outputs that are in phase with each other. This condition is readily achieved with finite-impulse response digital filters. To avoid aliasing, the sampling rate (i.e. the stimulation rate on that channel) must be at least four times the highest frequency that is passed by the band-pass filter. Aliasing is best avoided, because it introduces spurious frequency components.

Figure 15:
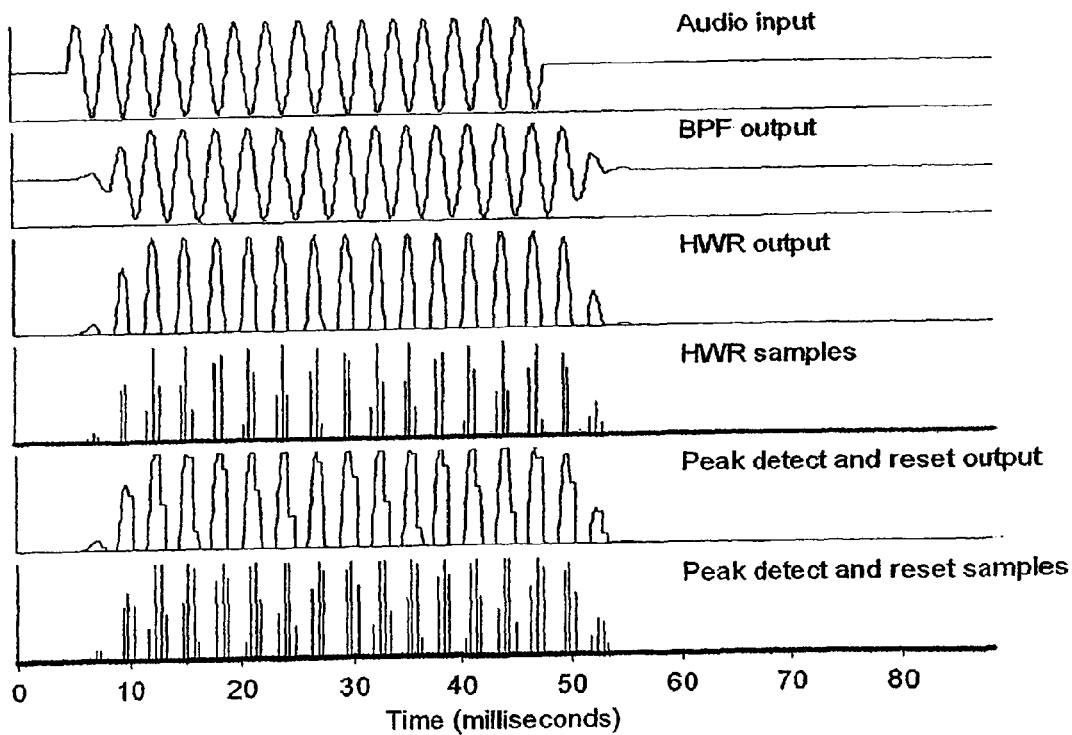
FIG. 15 is a graphical representation of signals associated with the circuit of FIG. 14.

The signals associated with this embodiment of the present invention are shown in FIG. 15. In this example, the audio input is a short burst of a 350 Hz pure tone, and the sample rate used is 2000 Hz (stimulation rate of 2000 pulses per second). There are several options for the electrical stimulation that results when the HWR output sample is zero. It can result in a stimulus pulse at the minimum current level (analogous to the CIS strategy). Alternatively, in a maxima selection strategy, this channel would not be selected for stimulation in this time interval (analogous to the ACE strategy).

To adequately represent the waveform, the sample rate (i.e. the stimulation rate on that channel) must be much higher than the highest frequency that is passed by the band-pass filter. Although the sample rate in this example is more than five times the audio frequency, it can be seen that the sampling introduces undesirable ripple. This ripple modulates at a beat frequency, which can give erroneous pitch cues to the implant recipient. Sample rates of at least eight times the audio frequency are preferred.

Figure 16:
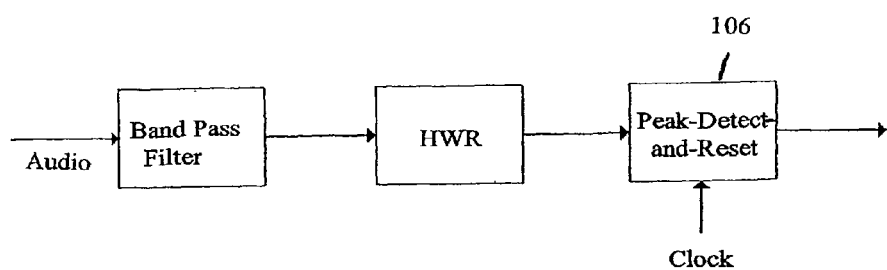
FIG. 16 is a block diagram of a further scheme for envelope detection but including a peak detect and reset stage.

Another embodiment of this aspect of the present invention is shown in the circuit 100 of FIG. 16. This embodiment utilises a peak-detect-and-reset stage 106 instead of a simple sample stage to reduce the ripple, as described previously. The signals shown resulting from this embodiment are shown also in FIG. 15.

As can be seen from the peak detected and reset samples (bottom illustration in FIG. 15), each group of samples that represent one of the half cycles of the HWR output now contains at least one sample that has the same amplitude as the HWR output.

Figure 17:
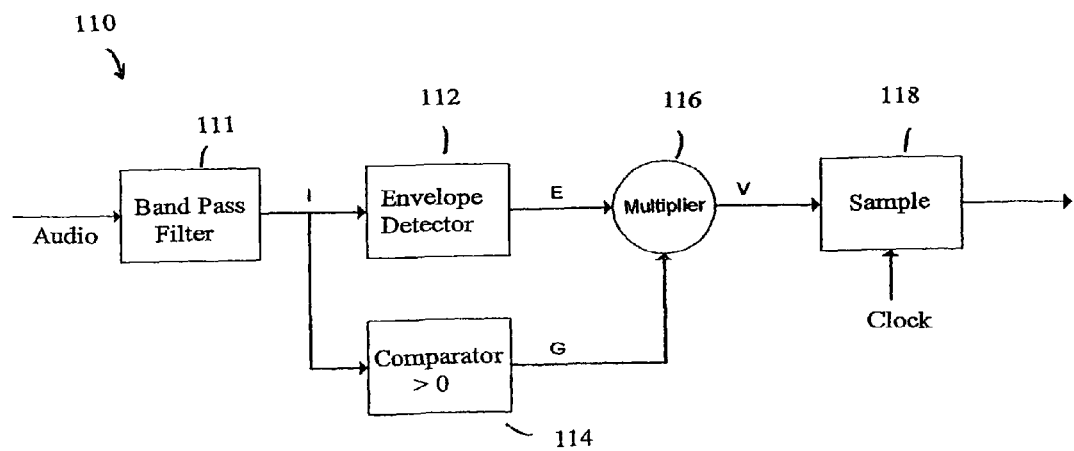
FIG. 17 is a block diagram of a circuit according to a further embodiment of the invention that enables enhanced pitch cue of an audio signal and includes a half wave gating arrangement.

Yet another alternative embodiment of this aspect of the present invention is shown in the circuit 110 of FIG. 17. This embodiment is referred to as half-wave gating (HWG). In FIG. 17, an envelope signal E is generated by an envelope detector 112 described in any one of the various prior art embodiments previously. A comparator 114 produces a Boolean gating signal G, which is high when the BPF 111 output is positive:

$$G=(I>0)$$

In other words, if I>0, then G=1 else G=0
The envelope signal E is then multiplied by the gating signal through multiplier or mixer 116, that is, the envelope is on-off modulated by the gating signal:

$$V=G*E$$

The signal V is then sampled by sample circuit 118.

Figure 18:
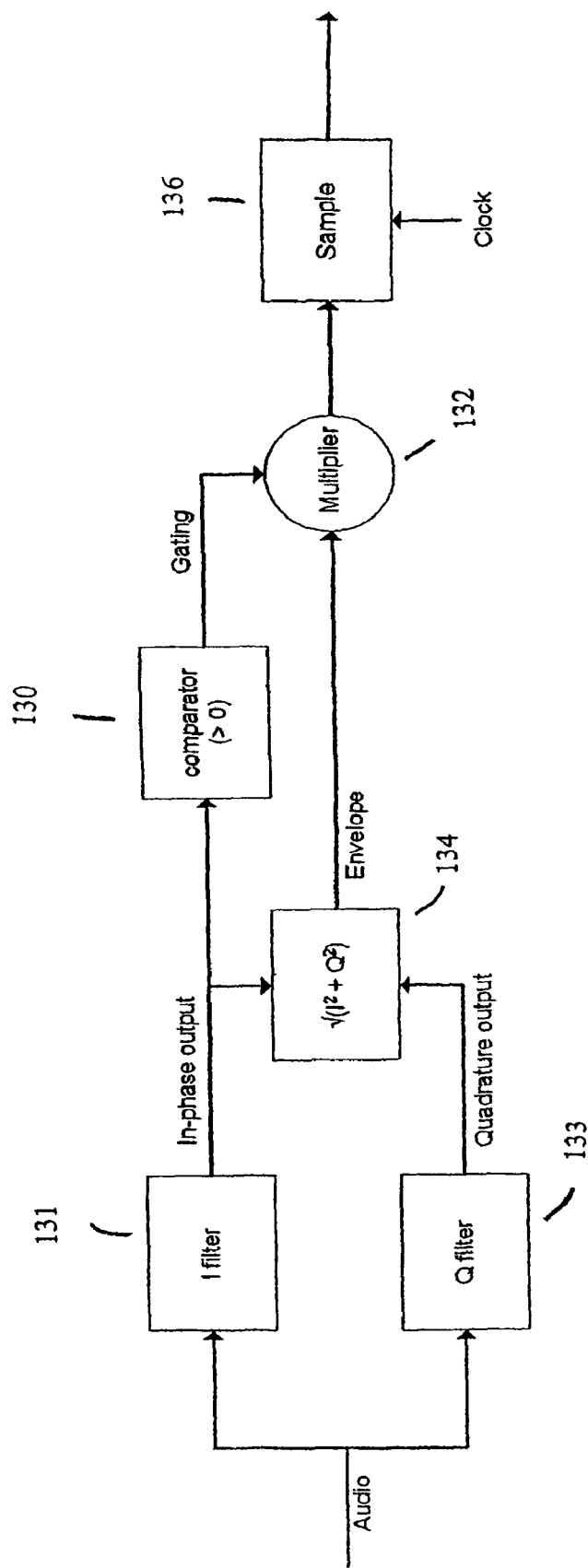
FIG. 18 is a block diagram similar to FIG. 17 wherein an envelope detection circuit is represented as a quadratic envelope detector.

The embodiment of FIG. 17 can be further described with reference to FIG. 18. In this example, the prior art quadrature envelope detector as discussed previously in relation to FIG. 8 is employed. However, that circuit is modified in FIG. 18 by having the In-phase output from I filter input to the comparator 130 whose output is fed to multiplier 132. Also, input to multiplier 132 is the envelop E output from square root function circuit 134. The output signal from multiplier 132 is then sampled by sampling circuit 136. The signals associated with this embodiment are shown in FIG. 19.

Figure 19:
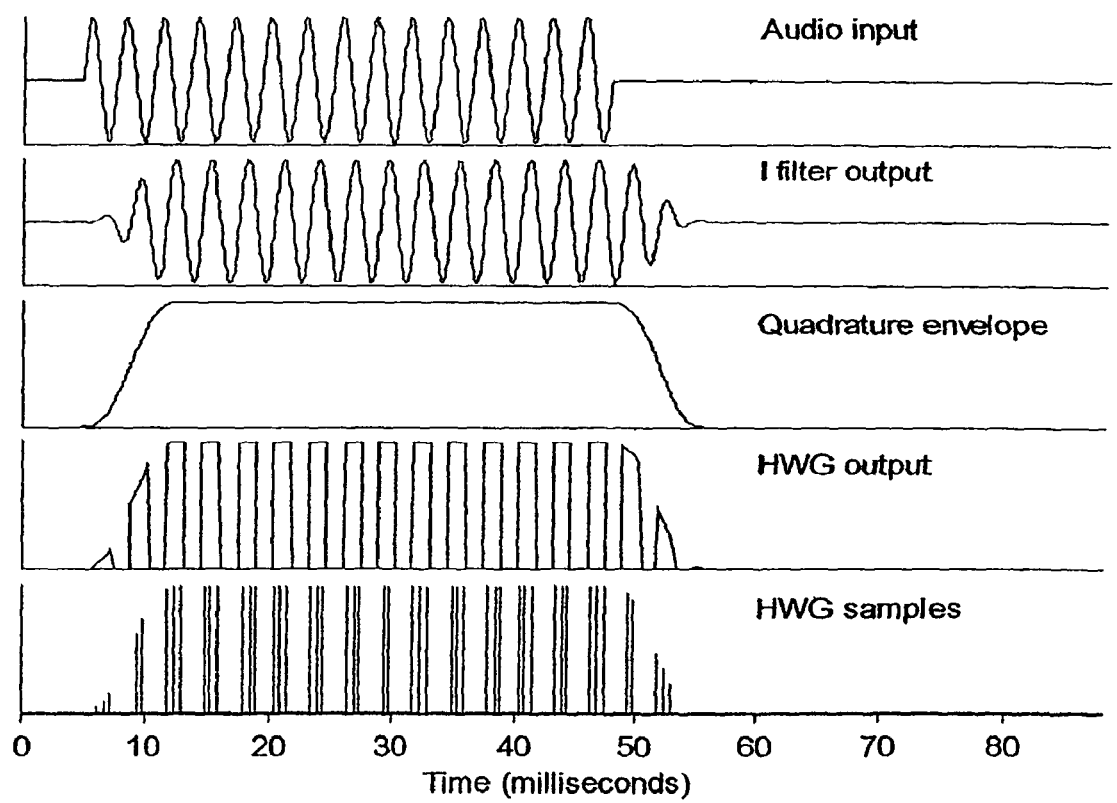
FIG. 19 is a graphical representation of signals associated with the circuit of FIG. 18.
Figure 20:
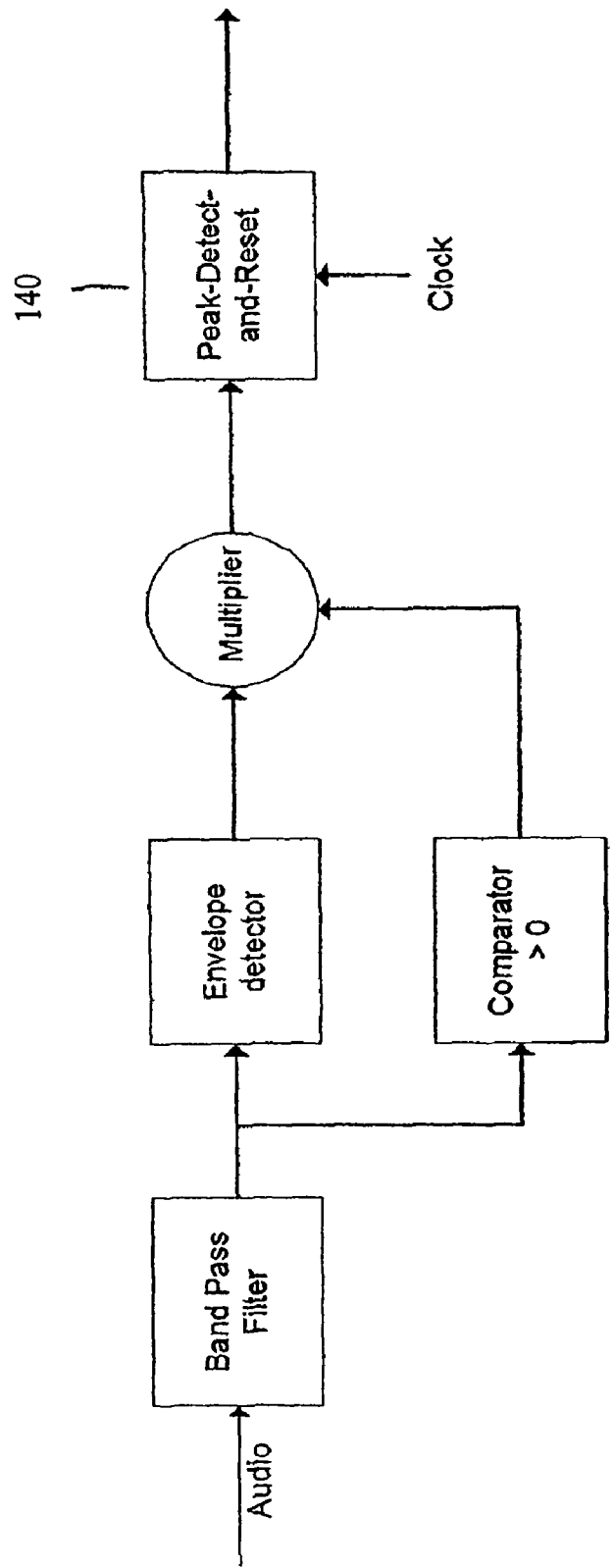
FIG. 20 is a block diagram of a circuit arrangement similar to FIG. 17 but including a peak detect and reset circuit.

The audio example shown in FIG. 19 is a 350 Hz tone burst as before. When the audio input has steady amplitude, the non-zero HWG samples all have the same amplitude, hence there is no amplitude ripple present. The main advantage of this form is that it does not need sample rates as high as the earlier HWR scheme, as it is essentially sampling the envelope signal, which varies more slowly than the BPF output. A sample rate of four times the highest audio frequency is adequate in this case, however for the high frequency channels it may be difficult to achieve a sample rate of at least four times the highest frequency that is passed by the band-pass filter. This constraint may be relaxed by using a peak-detect-and-reset stage 140, as shown in FIG. 20.

Figure 21:
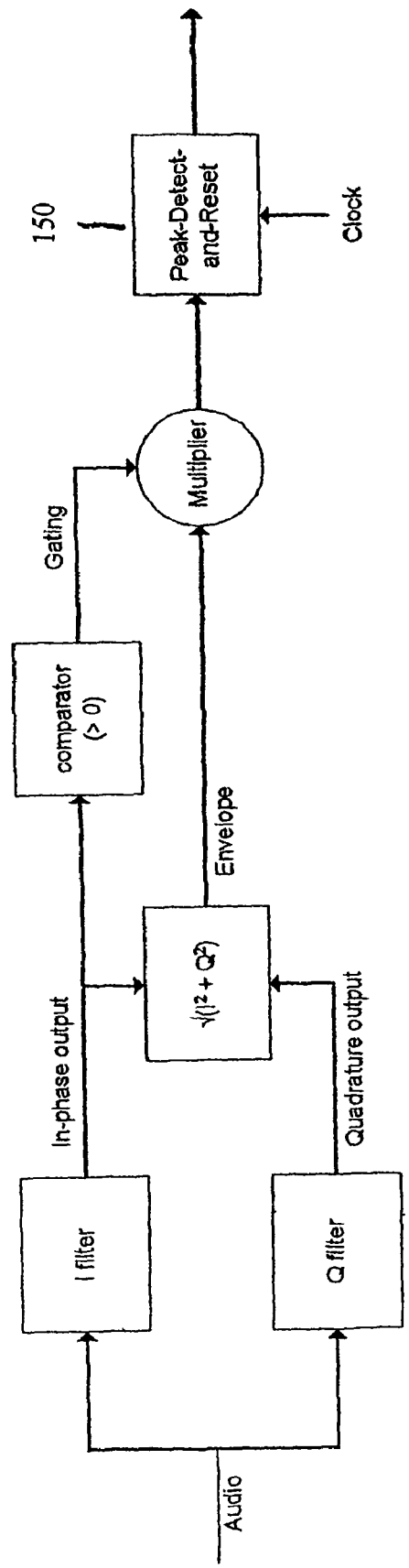
FIG. 21 is a block diagram similar to FIG. 20 where the envelope the detector circuit is represented as a quadrature envelope detector.
Figure 22:
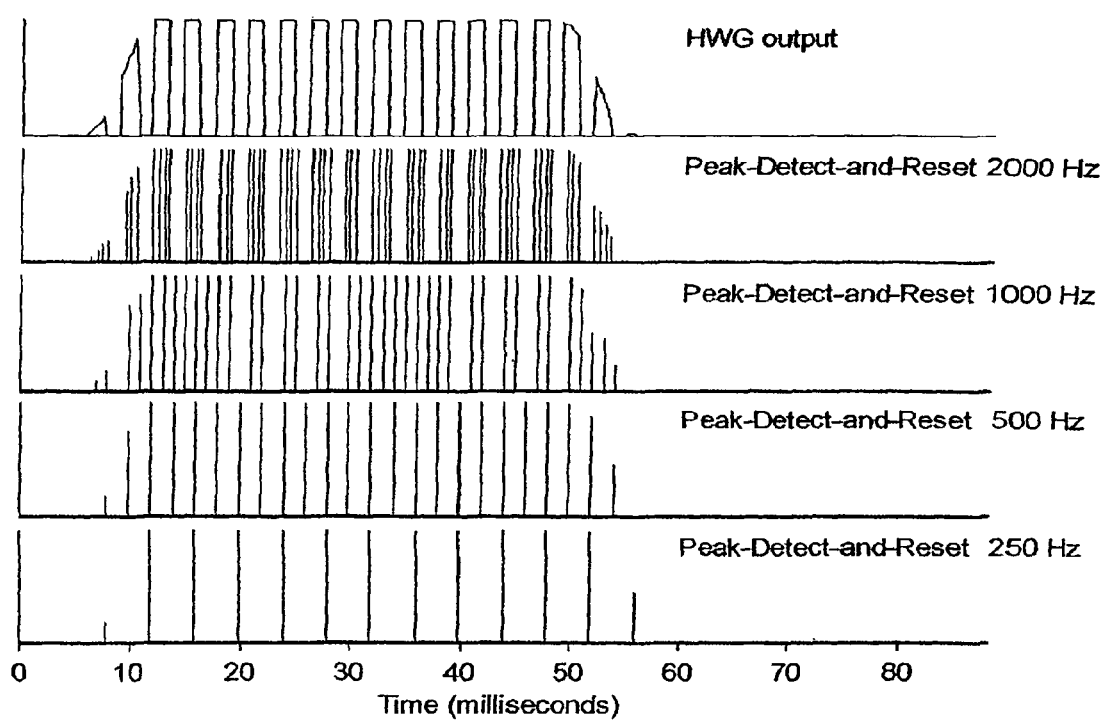
FIG. 22 is a graphical representation of the signals associated with the circuit of FIG. 21.

For the specific case of a quadrature envelope detector being used as the envelope detector, the peak-detect-and-reset stage 150 shown in FIG. 21 may be used. The signals from this specific embodiment of FIG. 21 are shown for four different sample rates in FIG. 22.

As can be seen, If the sample rate is more than four times the audio frequency, (in this example 2000 Hz) then the system acts as a half-wave gating system, and conveys the fine timing content of the BPF output, giving an enhanced pitch cue to the cochlear implant recipient. If the sample rate is less than twice the audio frequency (in this example 500 Hz or 250 Hz), then the system acts as an envelope detector, as in the prior art. For intermediate sample rates (in this example 1000 Hz), then it acts as an imperfect envelope detector, where samples are occasionally dropped. The perceptual consequences of this are minor, as it is similar to a timing jitter in the pulses that is sometimes implemented in the prior art. This system can thus be operated at a variety of stimulation rates without modification.

Furthermore, it is known that the phase-locking behaviour of the auditory nerves is most relevant for low audio frequencies (below 1000 Hz). Thus it can be advantageous to implement a cochlear implant system in which a Half-Wave detection scheme is used for the apical electrode channels (corresponding to low frequencies), and an envelope detection scheme is used for the basal electrodes (corresponding to high frequencies). Using a half-wave gating and peak-detect-and-reset on each channel will achieve this.

It may furthermore be advantageous to use a high stimulation rate on the apical channels (with a half-wave detection scheme) to obtain enhanced pitch cues; whilst using a lower stimulation rate on the basal channels (with an envelope detection scheme).

The third method of implementing the system of the present invention is a variation of the second method discussed above, but which addresses a problem associated with pitch perception present in the second method.

As discussed above, with reference to FIG. 19, the HWG samples (bottom waveform) have no amplitude ripple as is desirable in relation to the problems with prior art methods. The shown HWG samples essentially consist of bursts of pulses with approximately 50% duty cycle with the rate of burst generally equal to the audio frequency. However, because the sampling is not synchronised to the audio frequency, the bursts contain different numbers of pulses, in the example shown in FIG. 19 most bursts have three pulses but some bursts have only two pulses. Similarly, the interval between bursts varies.

Following a study of five cochlear implant recipients listening to pure tones processed by the above mentioned system, it was found that some reported hearing a "warble" in the perceived sound. In other words, instead of a steady pitch as desired, the pitch underwent small variations. It is believed that this is due to the pitch being at least partly dependent upon the interval between the bursts.

Figure 23:
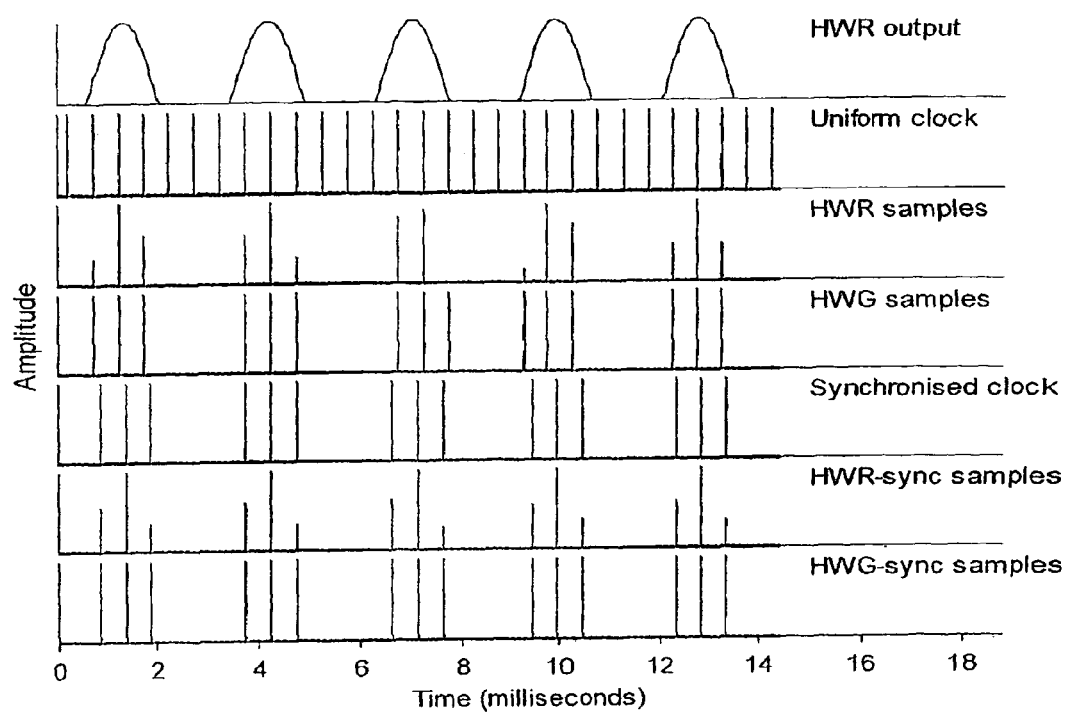
FIG. 23 is a graphical representation comparing the signals associated with a uniform clock versus a synchronised clock.

In this regard, the third method of implementing the present system is to synchronise the sampling clock with the audio waveform. FIG. 23 compares the HWR method of FIG. 15 and the HWG method of FIG. 19 with the third method, however in FIG. 23 the time scale has been expanded to better show the effects of synchronisation. The top waveform is the HWR output, before sampling. The next waveform is a uniform-rate clock. The next waveform shows the result of sampling the HWR waveform with the uniform clock which is the same as that shown in relation to FIG. 15. The next waveform shows the result of sampling the HWG waveform with the uniform clock which is the same as that shown in relation to FIG. 19.

The next waveform shows the synchronised clock of the present method. The synchronised clock consists of bursts of pulses and within each burst, the pulse rate is the same as the uniform clock. However, the leading pulse of each burst has been synchronised to the phase of the band-pass filter output. In this example, the leading pulse occurs a fixed time interval (one half of a clock period) after the rising zero crossing of the band-pass filter output.

The next waveform (HWR-sync samples) shows the result of sampling the HWR waveform with the synchronised clock. The HWR-sync samples occur in bursts of three pulses, and each burst has an almost identical set of amplitudes, because the samples have occurred in successive cycles of the band-pass filter output at the same phases. The HWR-sync samples therefore have much reduced ripple compared to the earlier HWR samples.

The final waveform (HWG-sync samples) shows the result of sampling the HWG waveform with the synchronised clock. The HWG-sync samples occur in bursts, where each burst has the same number of pulses (three), and the interval between successive bursts is constant. Again this is because the samples have occurred in successive cycles of the band-pass filter output at the same phases. Five cochlear implant recipients have listened to pure tones processed by this system, and they all reported a steady pitch. None of them reported hearing a "warble".

Figure 24:
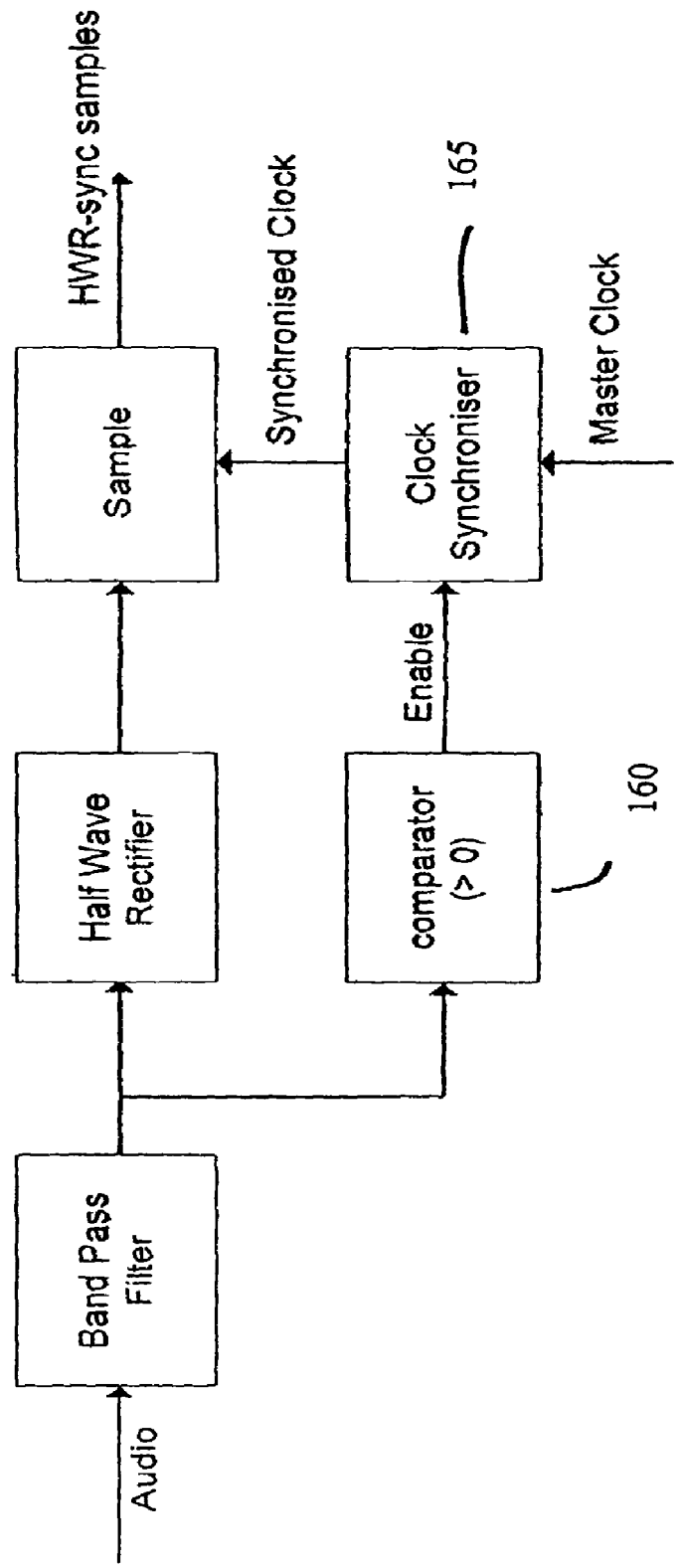
FIG. 24 is a block diagram of a circuit arrangement of the HWR-sync embodiment of the present invention.

FIG. 24 shows an implementation of the HWR with clock synchronisation as described above. Because the synchronised clock only takes samples when the waveform is positive, the half-wave rectifier is redundant and can be omitted. FIG. 25 shows an implementation of the HWG with clock synchronisation described above.

Each implementation uses a comparator 160 and clock synchroniser unit 165, with the latter being enabled only on positive outputs of the band pass filter using the comparator 160. In the implementation of FIG. 26 only the in-phase output from the I filter going positive is used by comparator 160 to enable the clock synchroniser unit 165.

The clock synchroniser is shown in FIG. 26. The master clock is a high frequency clock that determines the overall timing quantisation. A convenient choice is to set the master clock frequency equal to the total number of implant stimulation pulses per second. The enable signal is high when the band-pass filter output is positive, which then allows the clock to pass through the AND gate to the divide-by-N stage. This is a simple counter that outputs one clock pulse each time it receives N clock pulses. The divide-by-N stage is cleared when Enable is low, so that each new burst of clock pulses starts on the rising edge of Enable. As an example, the master clock frequency could be 14400 Hz (corresponding to a total implant stimulation rate of 14400 pulses per second), and the divider ratio N could be 8, so that synchronised clock has a burst rate of 1800 Hz (corresponding to a channel stimulation rate of 1800 pulses per second).

This system as described above, assumes that all channels are independent. This is applicable to a cochlear implant system that allows simultaneous stimulation on multiple channels. However, if the cochlear implant system only permits sequential stimulation, then an additional processing step is required to interleave the pulses amongst the channels. This is known as an Arbitrator.

The Arbitrator ensures that on each master clock pulse, no more than one channel has a low-to-high transition on its Enable signal. The Enable signals from each channel are the inputs to the Arbitrator. The Enable signals are passed through the Arbitrator with controllable delay on each channel. If more than one Enable signal goes high on a single master clock pulse, then one channel is selected, and is passed through immediately, but the remaining channels are delayed by successive master clock periods. In one embodiment, the Arbitrator prioritises the channels in order from low frequency to high frequency, so that the low frequency channels maintain the best synchronisation. In an alternative embodiment, the channels are prioritised in order of largest to smallest instantaneous amplitude. More complex rules using both frequency and amplitude can be devised.

It is considered that the present invention has significant advantages over the prior art envelope detection methods discussed previously. The present invention produces a more accurate envelope signal from each filter used in the processing strategy without the complexity and costs associated with quadrature envelope detectors. The implementation of the present invention will assist cochlear implant recipients to better perceive rapid changes in the amplitude of speech, particularly with respect to plosive consonants. Furthermore, the present invention provides implant recipients with enhanced pitch cue through the use of a half wave gating circuit arrangement at high stimulating rates whilst providing improved envelope detection at low stimulating rates.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of detecting an envelope of an audio signal comprising the steps of:
    filtering the audio signal to produce a filtered audio signal;
    rectifying the filtered audio signal to produce a rectified signal;
    detecting peak values of the rectified signal to produce a detected signal;
    sampling the detected signal, at a frequency that is less than the frequency components in the filtered audio signal, to produce samples; and
    resetting the detected signal immediately after sampling.

2. The method according to claim 1 wherein the rectifying step uses half wave rectification.

3. The method according to claim 1 wherein the rectifying step uses full wave rectification.

4. The method according to claim 1 wherein the detected peak values remain at a substantially constant value prior to the sampling step.

5. A method of detecting an envelope of an audio signal comprising the steps of:
    filtering the audio signal to produce a filtered audio signal;
    rectifying the filtered audio signal to produce a rectified signal;
    detecting peak values of the rectified signal to produce a detected signal;
    sampling the detected signal at predetermined time intervals to produce samples; and
    resetting the detected signal immediately after sampling;
    wherein the detected peak values remain at a substantially constant value prior to the sampling step; and
    wherein the detected signal or detected signals is reset substantially to zero.

6. The method according to claim 1 wherein the audio signal is input to a cochlear implant device.

7. A method of enhancing the pitch cue of an audio signal perceived by a cochlear implant recipient, wherein the audio signal is processed and input to an implant device of the recipient, the method comprising the steps of:

filtering the audio signal to produce a filtered audio signal;
half-wave rectifying the filtered audio signal to produce a half-wave rectified signal; and
sampling the half-wave rectified signal at a frequency greater than the frequency components in the filtered audio signal.

8. The method according to claim 7 wherein the sampling rate is at least eight times the highest frequency component in the filtered audio signal.

9. An apparatus for enhancing the pitch cue of an audio signal perceived by a cochlear implant recipient, the audio signal being processed and input to an implant device of the recipient, the apparatus comprising:
means for filtering the audio signal to produce a filtered audio signal;
means for half-wave rectifying the filtered audio signal to produce a half-wave rectified signal; and
means for sampling the half-wave rectified signal at a frequency greater than the frequency components in the filtered audio signal.

10. The apparatus according to claim 9 wherein the sampling rate is at least eight times the highest frequency component in the filtered audio signal.

11. An apparatus for enhancing the pitch cue of an audio signal perceived by a cochlear implant recipient, the audio signal being processed and input to an implant device of the recipient, the apparatus comprising:
means for filtering the audio signal to produce a filtered audio signal;
means for envelope detecting the filtered audio signal to produce an envelope detected signal;
comparator means for producing a gating signal having one of two Boolean states;
means for multiplying the gating signal with the envelope detected signal to produce a multiplied signal; and
means for sampling the multiplied signal at predetermined time intervals.

12. The apparatus according to claim 11 wherein the means for filtering uses an in-phase filter means and a quadrature filter means such that the audio signal is filtered respectively into in-phase and quadrature-phase filtered components.

13. The apparatus according to claim 12 wherein the means for envelope detecting uses quadrature envelope detection such that the envelope detected signal is produced using the in-phase and quadrature-phase filtered components of the audio signal.

14. The apparatus according to claim 13 wherein the gating signal is produced from an in-phase filtered component output from the in-phase filter means.

15. A method of enhancing the pitch cue of an audio signal perceived by a cochlear implant recipient, wherein the audio signal is processed and input to an implant device of the recipient, the method comprising the steps of:
filtering the audio signal to produce a filtered audio signal; and
sampling the filtered audio signal to produce samples;
wherein the samples are synchronized with one of positive phases and negative phases of the filtered audio signal.

16. A method of enhancing the pitch cue of an audio signal perceived by a cochlear implant recipient, wherein the audio signal is processed and input to an implant device of the recipient, the method comprising the steps of:
filtering the audio signal to produce a filtered audio signal; and
sampling the filtered audio signal to produce samples;
wherein the samples are synchronized with the filtered audio signal; and
wherein the sampling step uses a clock synchroniser that generates bursts of clock pulse separated by a fixed time interval with the leading pulse in each burst of pulses being synchronised to the phase of the filtered audio signal.

17. The method according to claim 16 wherein the leading pulse occurs at a fixed time interval after the rising zero crossing of the filtered audio signal such that only positive cycles of the filtered audio signal are sampled.

18. The method according to claim 17 comprising the steps of half-wave rectifying the filtered audio signal to produce a half-wave rectified signal and sampling the half-wave rectified signal.

19. An apparatus for enhancing the pitch cue of an audio signal perceived by a cochlear implant recipient, the audio signal being processed and input to an implant device of the recipient, the apparatus comprising:
means for filtering the audio signal to produce a filtered audio signal; and
means for sampling the filtered audio signal at predetermined time intervals to produce samples;
wherein the samples are synchronised with one of positive phases and negative phases of the filtered audio signal.

20. The apparatus according to claim 19 further comprising clock synchroniser means that inputs a clock signal to the sampling means, the clock signal comprising bursts of pulses separated by a fixed time interval with leading pulses in the bursts being synchronised to one of the positive phases and negative phases of the filtered audio signal.

21. The apparatus according to claim 20 further comprising comparator means that receives the filtered audio signal and outputs to the clock synchroniser means an enabling signal representative of positive cycles of the filtered audio signal.

22. The apparatus according to claim 21 wherein the leading pulse in each burst of pulses of the clock signal occurs at a fixed time interval after the rising zero crossing of the filtered audio signal such that only positive cycles of the filtered audio signal are sampled.

23. An apparatus for enhancing the pitch cue of an audio signal perceived by a cochlear implant recipient, the audio signal being processed and input to an implant device of the recipient, the apparatus comprising:
means for filtering the audio signal to produce a filtered audio signal; and
means for sampling the filtered audio signal at predetermined time intervals to produce samples;
wherein the samples are synchronised with the filtered audio signal; and
wherein the apparatus further comprises half-wave rectifying means connected between the filter means and the sampling means for half-wave rectifying the filtered audio signal to produce a half-wave rectified signal, and thereafter the sampling means sampling the half-wave rectified signal at predetermined intervals to produce samples that are synchronised with the filtered audio signal.

24. In a multiple channel cochlear implant system permitting sequential stimulation, a method of enhancing the pitch cue of an audio signal perceived by a cochlear implant recipient, wherein the audio signal is processed and input to an implant device of the recipient, the method comprising the steps of:
filtering the audio signal to produce a filtered audio signal;
sampling the filtered audio signal to produce samples; and synchronising the samples of the filtered audio signal using a selection means and a series of master clock pulses, such that on each master clock pulse no more than one channel is selected by the selection means.

25. The method according to claim 24 wherein each channel has a low to high transition on a channel enable signal.

26. The method according to claim 25 wherein each channel enable signal is input to the selection means and passed through the selection means with controllable delay on each channel.

27. The method according to claim 26 where more than one channel enable signal goes high on a single master clock pulse, the method further comprises the step of selecting one channel, with the remaining channels delayed by successive master clock periods.

* * * * *